United States Patent [19]

Williams

[11] Patent Number: 4,810,192

[45] Date of Patent: Mar. 7, 1989

[54] TWO-STAGE INTRA-ORAL PROTECTIVE SYSTEM

[76] Inventor: Edward D. Williams, 1432 Washington La., Philadelphia, Pa. 19138

[21] Appl. No.: 137,168

[22] Filed: Dec. 23, 1987

[51] Int. Cl.$^4$ .............................................. A61C 7/00
[52] U.S. Cl. ...................................................... 433/6
[58] Field of Search ...................... 128/76, 136; 433/6, 433/5

[56] References Cited

U.S. PATENT DOCUMENTS 4,672,959 6/1987 May et al. ........................... 128/136
4,727,867 3/1988 Knoderer ............................ 128/136

Primary Examiner—Robert Peshock
Attorney, Agent, or Firm—David Edwards

[57] ABSTRACT

A two stage intra-oral protective system is provided for protecting teeth, lips, and jaw from injury and/or for supporting the temporomandibular joint (TMJ) in a relatively fixed (stable) position thereby stabilizing the TMJ during head contact activity and/or permit the components of a TMJ disorder to be realigned for proper healing. Stage one is a mandibular orthodontic repositioning appliance and stage two is a mouth guard providing maxillary and mandibular teeth seats whereby the two stages harmoniously work together for protection and/or healing of the TMJ.

5 Claims, 2 Drawing Sheets

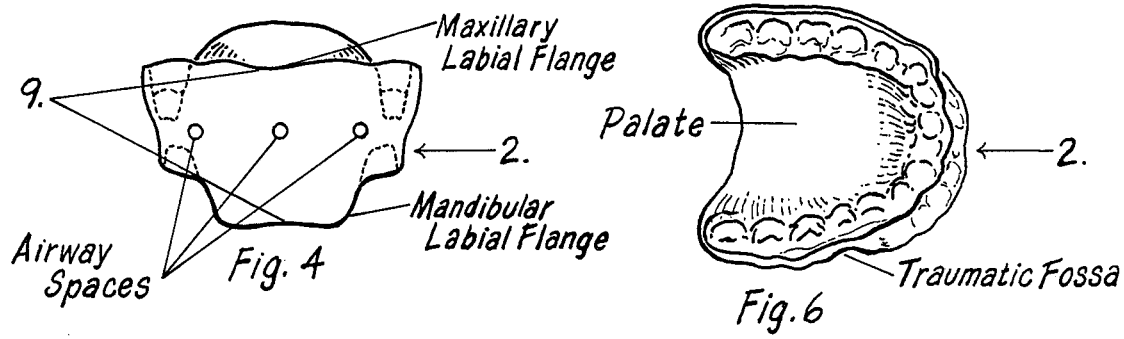
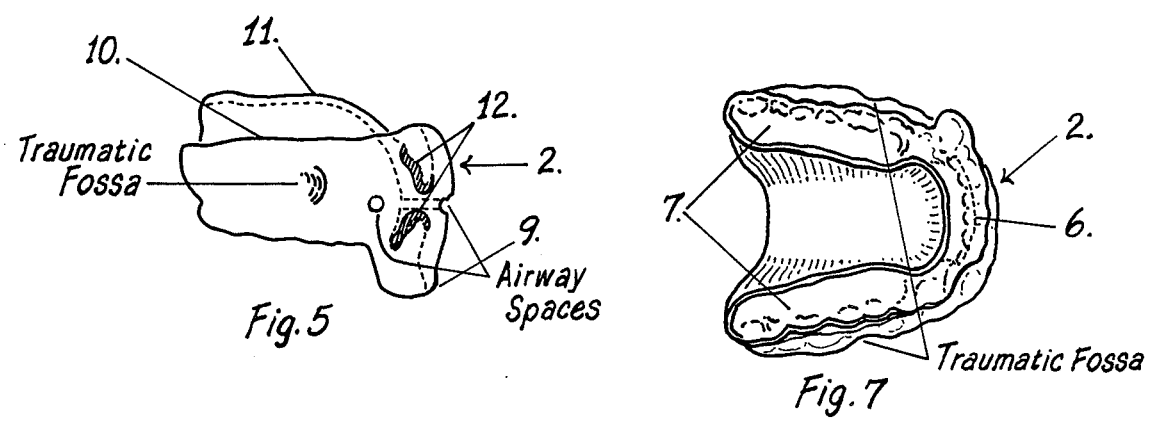
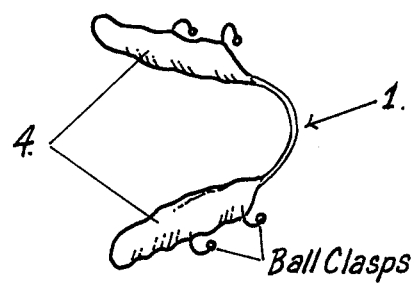
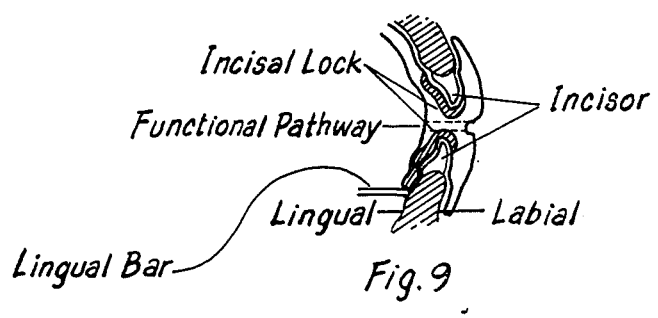

TWO-STAGE INTRA-ORAL PROTECTIVE SYSTEM

BACKGROUND OF THE INVENTION

This invention relates to a two-stage mouth guard for protecting teeth, lips, and jaw from injury and/or for supporting the temporomandibular joint (TMJ) in a relatively fixed position thereby stabilizing the TMJ during head contact activities and/or to permit the components of any TMJ disorders to be realigned for proper healing.

Prior to the present invention, disorders to the temporomandibular joint (TMJ) of the face have been overlooked and misdiagnosed. Although many rules and regulations in contact sports such as football, boxing, and contact karate exist for protecting the body, the TMJ of the face still needs adequate protection. The common mouth guard does little, if anything at all, to protect the TMJ. Although a high percentage of contact sport athletes have a TMJ disorder which is usually overlooked or taken lightly, it has been estimated that these disorders are more widespread with up to 50% of the population seeking dental treatment exhibiting some degree of TMJ dysfunction. The trauma produced n this joint has greater effects and manifestations than trauma produced in any other joint of the body. However, this is the most misdiagnosed, ignored, and untreated joint in the body. The seriousness of this joint is due to its anatomical structure, the approximation to the cerebral housing, and its functions. The gladiators, such as boxers, being the most proficiently trained in the administration of trauma to this delicate area, have created crippling injuries beyond imagination. The Health Profession must begin to focus its attention to treatment, care, maintenance, and prevention of injury to this joint and joint spaces.

TMJ dysfunctions are pathologic conditions of the craniomandibular articulation which affect mandibular opening, mastication, deglutition, and possibly other neurologic functions. A common type of dysfunction is internal derangement. A wide variety of causes exist for the TMJ dysfunction. It can be caused by a blow to the head, chin, or jaw due to a contact sport, an accident, attacks of violence, or just a simple fall. Stress, strain, tension, environmental pressure, and noise can also cause a mild dysfunction of the TMJ. The premature loss of teeth, especially the molar teeth, can cause disorders. It can be caused in infants by compression of the TMJ area at the time of child birth; this normally occurs by misuse of forceps by a doctor when pulling an infant down the birth canal of the mother.

Mild internal derangement of the TMJ may manifest itself in many symptoms, for example: pain around the neck, eyes, and ears, popping or clicking of the disc within the TMJ, clinching of facial muscles, grinding of teeth, malocclusion (i.e., teeth do not meet together well or meet improperly), ringing in the ears, notable rapid fatigue during physical activities, increased irritability, headaches of unknown origin, and the decrease of one's physical output.

One of the effects of the TMJ dysfunction is that the biting muscles of the jaw become sore which may cause other debilitating dysfunctions. If TMJ dysfunctions are not treated immediately, damage is often irreversible.

Many methods of treatment exist for correcting TMJ dysfunctions. One method of treating the TMJ dysfunctions is disclosed in U.S. Pat. No. 4,568,280; a craniomandibular appliance of a unitary insert of a remoldable thermoplastic material in the form of a dental arch is molded to the person's mouth in situ for positioning the mandible in a more forward position to obtain a reduced click or non-click condylar position. Another method of treatment or the TMJ disorders is disclosed in U.S. Pat. No. 4,671,766; a two-component intra-oral orthotic appliance with a wing on each component (where one fits in the maxillary arch and the other fits in the mandibular arch) is used to support the TMJ by closing the mouth so that the wing of each of the two components engages in a predetermined position to allow proper aligning of the TMJ for repair.

Neither of these patents discloses the instant invention.

SUMMARY OF THE INVENTION

The present invention is directed to a two-stage intra-oral therapeutic and protective device comprising a first stage adapted for securement within the mandibular arch of the mouth comprising a bilateral posterior bite table joined together by a lingual bar where the bite table has means for securing it to posterior teeth, and a second stage independent of the first stage comprising integrated maxillary and mandibular components where the components are adapted for securement within the full maxillary and mandibular arches of the mouth with stage one in place, the maxillary component comprising a reinforced anterior dental region, a bilateral posterior dental region, palate, and labial and buccal flanges and the mandibular component comprising a bilateral posterior dental region, a reinforced anterior dental region with a labial flange, and functional passages in the anterior of the integrated components, whereby the first and second stages fit congenially together in the mouth in working relationship for protecting the upper and lower teeth and holding the temporomandibular joint in its functional position.

BRIEF DESCRIPTION OF THE DRAWINGS

FIG. 4 is a frontal view of the second component (stage two) of the intra-oral protective device.

FIG. 5 is a side view of stage two of the intra-oral protective device.

FIG. 6 is a top plan sectional view of stage two of the device.

FIG. 7 is a bottom plan view of stage two of the device.

FIG. 8 is a plan view of stage one of the device.

FIG. 9 is a cross-sectional view of the reinforced anterior section of the device.

DETAILED DESCRIPTION OF THE INVENTION

Figure 1:
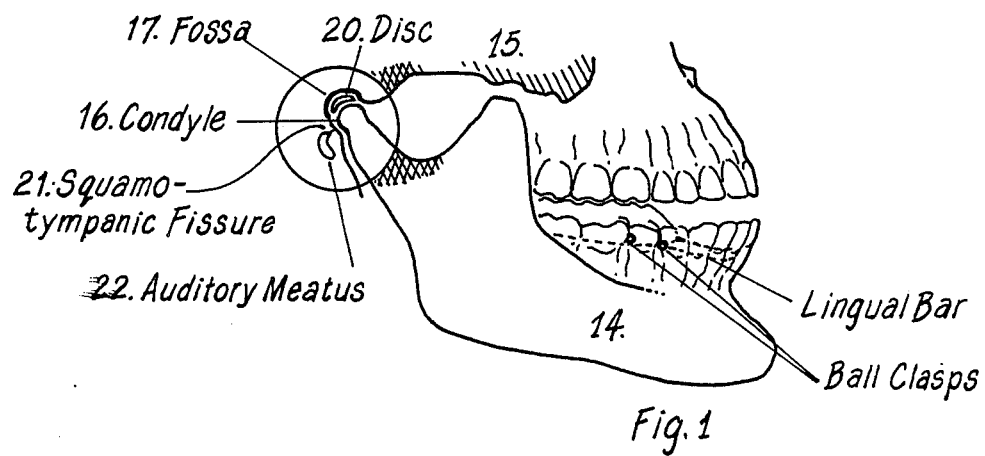
FIG. 1 is a partial side view of the skull showing the components of the functional change in the temporomandibular joint complex with stage one of the intra-oral protective device in place.

This invention is an intra-oral device composed of two stages denoted generally in the Drawings by numerals 1 and 2. Stage one (FIG. 8) fits in the mandibular arch of the mouth and stage two fits in the maxillary arch and mandibular arch with stage one in place. Stage one is a mandibular orthopedic repositioning appliance composed of a bilateral posterior bite table 4 supported by four ball clasps 3 for securing the bite table 4 to the posterior teeth and a lingual bar 5 that connects the bilateral bite table portions 4. FIG. 1 shows the functionally protected position of the TMJ complex with stage one in place. Stage one is normally worn continuously to promote healing and to stimulate constructive remodeling of the injured condyle-fossa complex. The construction and thickness of stage one is dependent upon one's physiological functions and radiographic interpretation of the condyle-fossa complexity.

Stage two (FIGS. 4, 5, 6, and 7) is composed of a reinforced anterior dental region 6 and bilateral posterior dental regions 7 where the maxillary and mandibular teeth are functionally seated having labial border 9 and buccal border 10 and a palatal portion 11 ending just before the soft palate of the mouth. The labial-buccal borders 9 and 10 are carried high into the muccobuccal fold of the mouth avoiding impingement of the labial frenums and posterior muscle attachments. FIG. 5 shows that the lingual surface 12 is reinforced behind the maxillary anterior teeth from canine to canine; likewise, the lingual mandibular flange area is reinforced in the anterior from canine to canine. The palate portion 11 is carried high onto the hard palatal section of the mouth terminating generally just anterior to the soft palate of the mouth. Traumatic fossa 13 is an indentation located generally in the premolar region of stage two for quick removal from an unconscious gladiator. The thumb and the second finger are placed in the indentations of the fossa 13 for quick removal in an emergency.

FIG. 9 shows a cross-sectional view of the anterior with the acrylic reinforcement of stage two starting from its incisor lock to the soft tissue of the gingiva on the lingual surface.

In the mandibular teeth section of stage two the anterior lingual mandibular flange is designed to terminate at the lingual bar 5 to provide comfort to the tongue position and a more compatible fitting of the two stages. Starting at the mesial of the first premolar, the labial border of the mandibular section is cut back to the crest of contour of the mandibular posterior teeth. This is designed so that stages one and two fit congenially in the mouth in a supportive role with greater retention in the maxillary arch. With the mandible placed in a functionally protruded position, the mandibular and maxillary units are integrated into one unit. The integration is governed by the placement of stage one unit, the kinesiologically functional physiology, the condyle-fossa physiology, and the functional free-way space.

FIG. 1 shows the components that comprise the TMJ complex. This joint includes two primary bones, the mandibular bone 14 which articulates with the temporal bone 15 as a ball (condyle 16) and socket (fossa 17) joint. There is a cushion between the condyle 16 and the fossa 17 called the meniscus or disc 20. The squamotympanic fissure 21 and the auditory meatus 22 are also shown in conjunction with the TMJ complex.

In the case of internal derangement of the TMJ, the position of the condyle is displaced (generally superiorly and distally) to such an extent that the articular disc may be displaced from, herniated from, or torn from its normal position. This not only affects the intracapsular system, but may also interfere with the ability to move the mandible in a normal fashion. In addition to the many discomforts this may cause in connection with talking, eating, and other activities, it may also impose a strain on the muscles associated with the mandible, head, neck, and vetebral column. This strain or resulting spasm may be severe enough as to cause patient discomfort or even significant physical and neurological impairment.

Figures 2, 3:
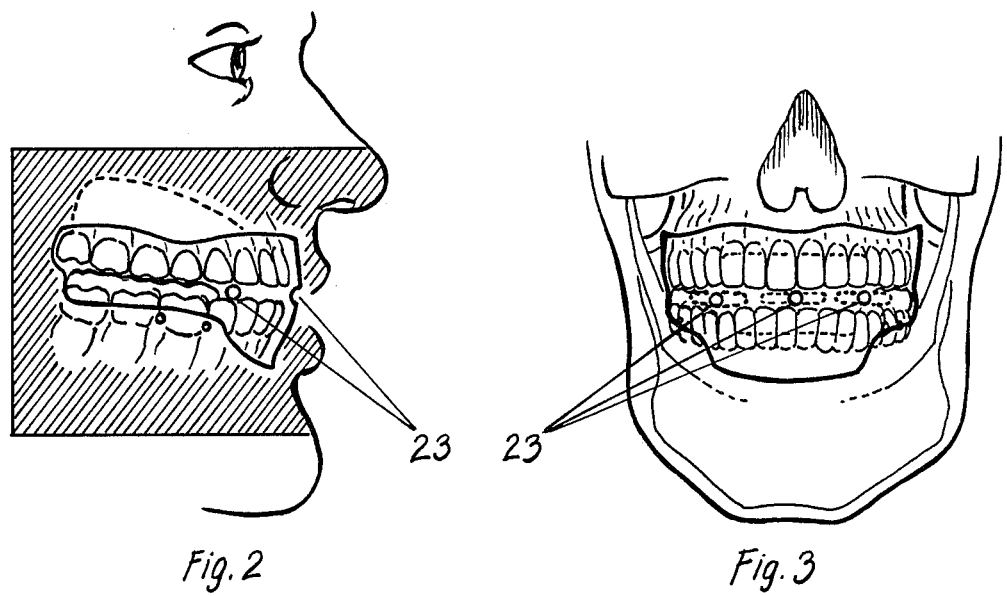
FIG. 2 is a side sectional view of the mouth showing the relationship of the intra-oral protective device stages.
FIG. 3 is a sectional frontal view of the mouth showing the airway spaces or expectorant orifices in the intra-oral protective device.

FIGS. 2 and 3 show that the design of the intra-oral protective device is such that the upper and lower dental arches are held in a spaced-apart position of desired dimensions with airways (or saliva orifices) so that the gladiator wearing the device can readily breathe or expectorate, depending on the activity.

The bite table of stage one is normally made of a heavy duty plastic material such as acrylic that can withstand pressure, is easily molded, and is inert to the mouth chemistry of the person (or gladiator) wearing it. Rubber is used for producing mouth guards of stage two which rubber must be heavy duty, non-toxic, and inert which would be well known to a person in this art. In stage one, a metal which is compatible with the body chemistry of the user is used for the lingual bar for connecting the bilateral acrylic bite table portions together. Other materials for the device that meet the specifications of the American Dental Association for intra-oral use would be known to a person in the art.

Comparative functions of the intra-oral protective device (called Williams Intra-oral Protective Sports System (WIPSS)) of the present invention to the conventional mouth guards are as follows:

| DESCRIPTION | WIPSS | CONV. |
| --- | --- | --- |
| 1. absorbs the shock and protects max. dentition | yes | yes |
| 2. absorbs the shock and protects mand. dentition | yes | no |
| 3. eliminates compression of the disc of the TMJ | yes | no |
| 4. eliminates compression of condyle-fossa space | yes | no |
| 5. promotes healing of condyle-fossa complex while the athlete participates actively in sports | yes | no |
| 6. promotes healing of condyle-fossa complex while the athlete is at rest | yes | no |
| 7. facilitates remodeling of injured condyle-fossa relationship | yes | no |
| 8. increases functional physical output of the athlete | yes | no |
| 9. greater stability against traumatic dislodgement | yes | no |
| 10. decreases trauma to the anterior component of the tongue | yes | no |
| 11. increase in safety, medical supervision, and diagnostic evaluation | yes | no |
| 12. decrease in the incident of lip injuries "the tooth through lip syndrome" | yes | no |

What is claimed:

1. A two-stage intra-oral therapeutic and protective device comprising a first stage adapted for securement within the mandibular arch of the mouth comprising a bilateral posterior bite table having posterior occusal bite plates supported with lingual flanges joined together by a lingual bar where the bite table has means for securing it to posterior teeth wherein the rigidity of the first stage prevents all adverse posterior movement of the condyle from impinging upon previously damaged areas of temporomandibular joint, and a second stage independent of the first stage comprising integrated maxillary and mandibular components where the components are adapted for securement within the full maxillary and mandibular arches of the mouth with stage one in place, the maxillary component comprising a reinforced anterior dental region, a bilateral posterior dental region, palate, labial flange, and buccal flange, and the mandibular component comprising a bilateral posterior dental region, a reinforced anterior dental region with a labial flange, and functional passages in the anterior of the integrated components, whereby the first and second stages fit congenially together in the mouth in working relationship for protecting the upper and lower teeth and holding the temporomandibular joint in its functional position.

2. The device of claim 1 wherein the means for securing the bite table to posterior teeth are ball clasps.

3. The device of claim 1 where the functional passages are always or expectorant orifices.

4. The device of claim 1 where stage two has a pair of traumatic fossa in the buccal surface of the posterior region of the stage for rapid removal of said stage from an unconscious user.

5. A method of treating a temporomandibular joint disorder by a person having such a disorder wearing the device claim 1 when participating in athletic activity or when in need to correct such disorder by holding the temporomandibular joint stable and in its functional position for a sufficient time period in order to afford protection and healing thereof.

* * * * *